United States Patent
Ehlinger

Patent Number: 5,498,319
Date of Patent: Mar. 12, 1996

[54] PROCESS FOR PURIFYING DIARYL CARBONATES

[75] Inventor: Robert B. Ehlinger, Waterford, N.Y.

[73] Assignee: General Electric Company, Pittsfield, Mass.

[21] Appl. No.: 84,647

[22] Filed: Jun. 29, 1993

[51] Int. Cl.⁶ .............................. B01D 3/14; C07C 69/96
[52] U.S. Cl. ................. 203/39; 203/94; 203/98; 558/274
[58] Field of Search ................... 203/39, 94, 98, 203/91, 95; 558/274, 271

[56] References Cited

U.S. PATENT DOCUMENTS

| | | | |
|---|---|---|---|
| 2,362,865 | 11/1944 | Trgon et al. | 558/274 |
| 3,470,133 | 9/1969 | Ohme | 528/490 |
| 4,013,702 | 3/1977 | Cartier et al. | 528/196 |
| 4,697,034 | 9/1987 | Janatpour et al. | 558/274 |
| 5,167,946 | 12/1992 | Mullins et al. | 558/274 |
| 5,189,139 | 2/1993 | Tuinstra et al. | 528/198 |

OTHER PUBLICATIONS

CA 98(4): 17502m, 1993; Teijin Chemicals.
CA 85(22): 161161y; 1993, Cartier.
CA 97(10): 73376q.
CA 93(24): 221307c; 1993, Govoni et al.
CA 92(4): 23516m, 1993 Mori et al.
EP 44510 Abstract.
CA 106(2): 6063b; Chichet K. et al.
CA 104(18): 150063c; Sei et al.

*Primary Examiner*—Virginia Manoharan

[57] ABSTRACT

Illustrated by the purification of diphenyl carbonate (DPC), diaryl carbonates are purified and freed of contaminants such as inorganic and organic chlorides, metal ions, iron components and color bodies. The process is a two-stage procedure starting with a water wash of the molten carbonate followed by distillation. Crude DPC is charged to the wash tank and is washed in the molten state three times. Fresh steam condensate is used for each wash which consists of a period of agitation followed by decantation then water removal. After the third wash, the molten DPC is transferred to a still for distillation. The rag layer which is formed at the water/DPC interface during washing is purged and not allowed to pass through to the still. A flash distillation is carried out under constant vacuum. Three overhead cuts are taken—lights, intermediate and product DPC depending on the temperature of the overhead vapor.

8 Claims, 1 Drawing Sheet

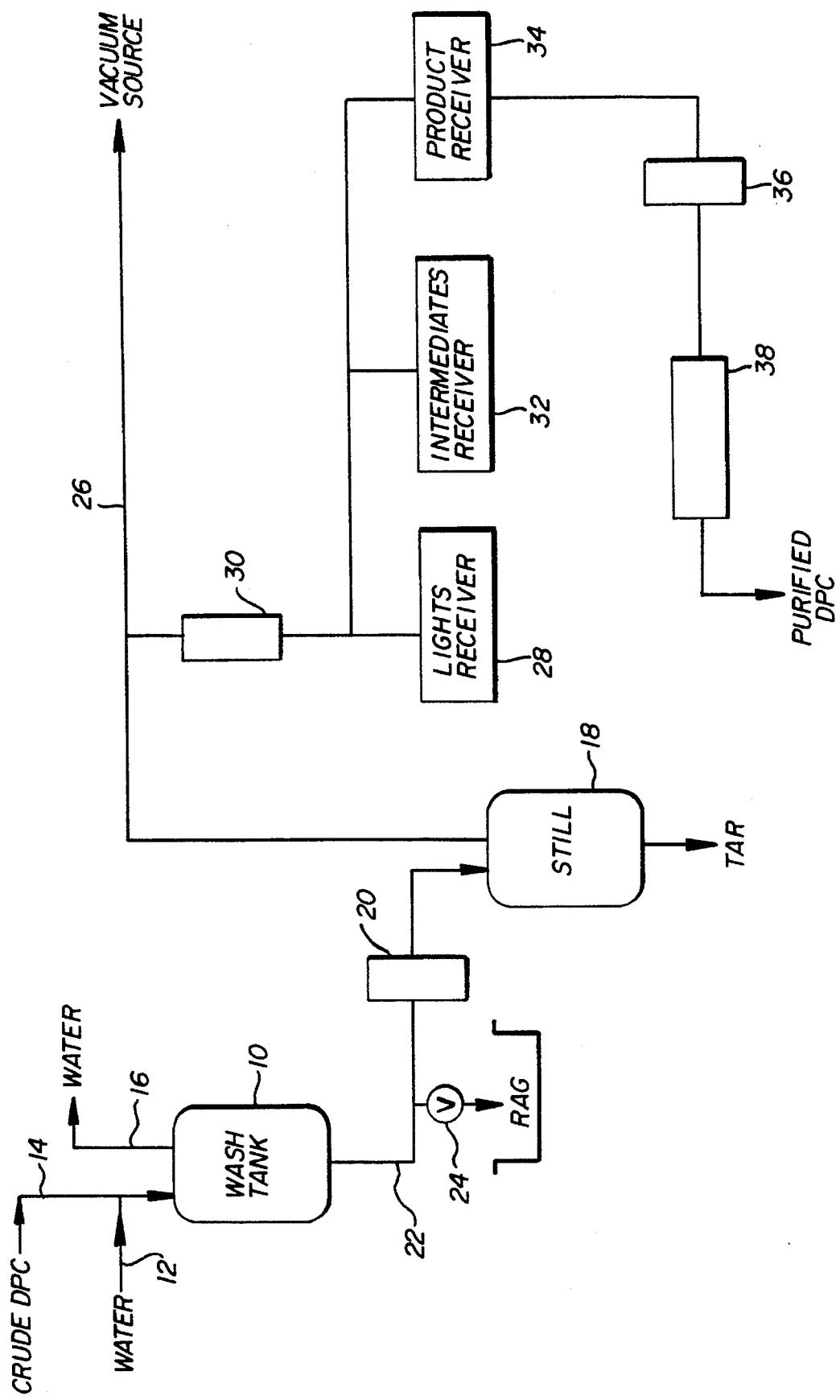

PROCESS FOR PURIFYING DIARYL CARBONATES

BACKGROUND OF THE INVENTION

1. Field of the Invention

The invention relates to processes for the purification of diaryl carbonates such as diphenyl carbonate.

2. Brief Description of the Prior Art

Diaryl carbonates such as diphenyl carbonate may be prepared by a number of processes. For example, one process is based on the phosgenation of aromatic hydroxy compounds in the presence of a quaternary ammonium salt catalyst. A variant process comprises phosgenation at elevated temperatures in alkaline solution. A commercial process for production of diphenyl carbonate comprises phosgenation of phenol in the presence of caustic at a pH of 10–11 and at a temperature of 55°–60° C.

Commercial preparations of the diaryl carbonates, regardless of the process employed, inevitably contain various contaminant compounds in varying quantities. Examples of contaminants which have been identified are inorganic and organic chlorides, metal ions, iron compounds, acidic compounds such as aryl chloroformates and a range of compounds identified only as "color bodies". These contaminants frequently effect use of the diaryl carbonates in particular applications. For example, when their desired use is as a monomer reactant in the preparation of aromatic polycarbonate resins by transesterification (using bisphenol-A and diphenyl carbonate), presence of the contaminants can affect polymerization rates and resin color. The polymer product may have a low intrinsic viscosity (IV) and colors ranging from pink (iron contamination) to brown (phenyl chloroformate contamination).

Although distillation of diaryl carbonates has been useful to remove color bodies and solves the problem of coloration in the carbonate and resins prepared from them, the procedure has not been useful to remove other contaminants responsible for inhibiting polymerization rates. In fact, a major drawback of distilled diphenyl carbonate is a loss of reactivity as observed in ester interchange reaction studies. The reason is open to speculation. Also, subjecting the diaryl carbonate, such as diphenyl carbonate, to distillation solely as a means of purification results in a percentage of product loss, which is an economic disadvantage.

We have found that relatively crude diaryl carbonate containing contaminants associated with the process of preparation may be purified advantageously by a two-stage procedure to optimize overall yield of the desired product and remove contaminants. The first stage is washing a melt of the diaryl carbonate with water; followed by a second distillation stage. An intermediate cut taken during distillation between the first and last (product) cuts helps to isolate color bodies and contaminants responsible for producing low intrinsic viscosity and/or colored polymer resins therefrom.

The distilled product is of improved reactivity and high purity, when the distillation procedure is immediately preceded by a hot aqueous wash in accordance with the method of the invention. Water washing of the crude diaryl carbonate helps reduce the content of contaminants including iron, and improves final color in polymers prepared from the purified diaryl carbonate.

The process of the invention may be carried out to purify diaryl carbonates in a continuous or a batch procedure, with an advantage in that the product is consistently obtained in high purity.

SUMMARY OF THE INVENTION

The invention comprises a process for purification of diaryl carbonates, which comprises;
washing a melt of the diaryl carbonate with water; and
distilling the washed diaryl carbonate.

BRIEF DESCRIPTION OF THE DRAWING

The accompanying drawing is a schematic flow chart showing a preferred embodiment process of the invention.

DETAILED DESCRIPTION OF THE PREFERRED EMBODIMENTS OF THE INVENTION

The following description will be directed to a preferred embodiment process of the invention for purification of diphenyl carbonate (DPC). Those skilled in the art will appreciate that the inventive process is applicable to purification of other diaryl carbonates, such as for example, di-ortho-cresyl carbonate, di-ortho-chlorophenyl carbonate and the like.

With reference to the accompanying drawing there is seen schematically a preferred embodiment process of the invention. Wash tank 10 is charged with hot water having a temperature sufficient to melt the diphenyl carbonate (circa 75°–95° C.; preferably about 80° C.) inserted through the line 12 from a source. The water charge is maintained at the elevated temperature while crude diphenyl carbonate is added by insertion through line 14. The crude diphenyl carbonate is melted in the hot water. Advantageously air in wash tank 10 is purged with an inert gas such as nitrogen and the tank 10 contents agitated at a temperature of circa 75°–95° C. for a period of time sufficient to extract metal ions, iron compounds and organic and inorganic chlorides from the molten diphenyl carbonate. In general, from 5 to 30 minutes time is sufficient. At the end of this time period, the mixture may be allowed to stand for a period of time sufficient to allow the phases to separate (5 to 15 minutes or more). The water phase is then removed from the wash tank 10 through line 16. In most preferred embodiment processes of the invention, fresh hot water is then introduced into the wash tank 10 for repeated washings following the wash procedure described above. Generally 2 to 4 washings are advantageous, preferably 3. At the completion of washing, the diphenyl carbonate melt is transferred to a distillation unit or still 18, passing first through a filter 20. Advantageously, a filter which will remove solid impurities having a size of 10 microns or less is used. During the washing, a rag layer forms at the water/diphenyl carbonate interface. This layer may be purged from the process system prior to filter 20 in the conduit 22 through a by-pass valve 24 when observed by its dark color through a sight glass in conduit 22. The amount of rag layer is roughly proportional to the iron content in the crude diphenyl carbonate. The iron appears to concentrate in the rag layer.

According to the preferred invention flash distillation under constant vacuum is carried out in still 18. Vacuum is advantageously pulled down to circa 5 to 40 mm Hg through vacuum line 26, while heating the molten diphenyl carbonate to a distillation pot temperature of not more than about 180° C., preferably circa 180° C. Three overhead cuts are taken (lights, intermediate and product diphenyl carbonate) depending on the temperature of the overhead vapor. The lights cut (phenol) is taken into receiver 28 from condensor 30 as long as the overhead vapor temperature is less than about 180° C. When the vapor temperature reaches 180° C., the still 18 pot temperature is raised to 210° C. and the second or intermediate cut is taken into receiver 32. The intermediate cut consists mainly of partially purified diphenyl carbonate and is taken to improve purity of the final cut. The intermediate cut is advantageously recycled through a later batch of crude diphenyl carbonate, to improve overall yields. The separation of the intermediate cut for further washing and distillation through recycle in a subsequent batch serves to isolate color bodies and unidentified compounds which apparently effect polymerization of the monomer diphenyl carbonate product (results in low intrinsic viscosity polycarbonate resins). Advantageously, the intermediate cut is taken until about 5 to 20 percent of the theoretical amount of diphenyl carbonate to be purified is recovered in the intermediate cost. This generally occurs within a period of about 1 hour. At the end of this time, the still 18 pot temperature may be raised to circa 220° C. and the third or final cut taken into an agitated receiver 34. The final cut of high purity diphenyl carbonate is taken until the overhead vapor temperature drops below a temperature of about 180° C. or rises above a temperature of about 190° C. The overhead vapors are condensed in condensor 30 which is advantageously maintained at a temperature of circa 90° C. during the distillation procedure.

After all of the diphenyl carbonate coming over in the third cut is collected, distillation is terminated by breaking vacuum. The still 18 pot residue (tar) may be evacuated from the still 18 and the molten diphenyl carbonate from receiver 34 filtered, through filter 36, cooled to solidify and flaked on a flaker 38 to obtain the final product of high purity.

Distillation of diphenyl carbonate was previously carried out at temperatures of circa 300° C. under atmospheric pressures. We have discovered that these conditions are actually degradative of the desired diphenyl carbonate product, particularly when the diphenyl carbonate has been washed as described above. The detrimental effects of high distillation temperatures are temperature and, to some degree, time dependent. (e.g. 150° C., 5 hrs no significant detrimental effects; 200° C., 5 hrs results in color degradation and loss of purity (diphenyl carbonate content). Accordingly, the method and process of the present invention preferably includes critical temperature parameters to avoid thermal ageing of the desired product.

The following examples describe the manner and process of carrying out the invention and set forth the best mode contemplated by the inventor, but are not to be construed as limiting the scope of the invention. Where indicated, the quality of the diphenyl carbonate prepared is measured indirectly on polymer made from the diphenyl carbonate by a transesterification reaction. The transesterification reaction is carried out by mixing equal weights (228 gm) of diphenyl carbonate and bisphenol A with 1 ppm of a catalyst in a 1 liter flask. The flask is agitated while being purged with nitrogen gas, then heated under vacuum until no phenol comes off. The polymer color is visually measured. The intrinsic viscosity (IV) is measured at a temperature of 25° C. in methylene chloride and is reported in deciliters/gram (dl/g). An acceptable IV is considered to be 0.5 or above.

EXAMPLES 1–3

Using the process described above in relation to the accompanying drawing, 3 batches, (each batch being 800 lbs. of crude diphenyl carbonate) were first washed and then the washed product was distilled. Example 1 received 1 washing, Example 2 received 2 washings and Example 3 received 3 washings. The following procedure and conditions were used.

Water Washing

1. Add 100 gallons of 80° C. water (steam condensate) to wash tank (10).
2. Load 800 lbs. of crude DPC into wash tank (10). Maintain the DPC/water mixture temperature at 80° C. by adjusting the tank (10) jacket temperature.
3. Start nitrogen purge and agitation of the tank (10) content.
4. Agitate for 20 minutes after temperature reaches 80° C. Turn off agitator. Let mixture stand for 10 minutes. Blow off the water phase through a dip pipe by pressurizing the tank (10) with nitrogen.
5. For additional washes as in Examples 2 and 3, the procedure was repeated by adding 100 gallons of fresh 80° C. water to wash tank (10), and repeating steps 3–4 one or two more times.
6. Transfer the DPC melt to a still (18) by pressurizing the wash tank (10) with nitrogen and opening the product valve (24) off the wash tank (10). Watch the sight glass for rag layer.
7. When rag layer (dark layer) is seen in the sight glass, shut product valve and open the water drain valve (24). Drain the rag layer. Do not let the rag layer pass into the still (18).

The effect of washing was studied by varying the number of water washes from one to three. Reuse of the water was also explored by reusing the second wash water from one batch as the first wash for the next batch (but not in Examples 1–3, supra.). In general for the chloride levels in the crude (6.6–7.0 ppm) with either 1–3 washes or reuse of the water, the titratable chloride in the DPC was reduced to 1 ppm. Chloride levels in the water were highest in the first wash and were reduced with each successive wash. Iron was at 5.3–7.1 ppm in the crude and was reduced with each successive wash both in the DPC and in the water. These results are summarized in Table 1 below.

TABLE 1

| | Effect of Water Washing | | |
| --- | --- | --- | --- |
| | DPC Contaminants | | |
| | Crude | After Washing | In Final Wash Water |
| EXAMPLE 1 (1 wash) | | | |
| Cl | 6.6 ppm | <1 ppm | 4.1 ppm |
| Fe | 5.6 | 2.5 | 0.4 |
| EXAMPLE 2 (2 washes) | | | |
| Cl | 7.0 ppm | <1 ppm | 2.9 ppm |
| Fe | 5.3 | 2.0 | 0.2 |
| EXAMPLE 3 (3 washes) | | | |
| Cl | 7.0 ppm | <1 ppm | 1.0 ppm |
| Fe | 7.1 | 1.3 | 0.1 |

Reusing wash water accumulates iron and chloride in the wash water. The color of the polymer made from DPC washed 1–3 times with fresh water washes was successively better with each wash. When wash water was reused, polymer color worsened as the accumulation of iron and chloride increased.

Distillation

1. Raise temperature of still (18) pot before pulling vacuum. (Jacket should be circa 200° C.).
2. Pull vacuum down to 20 Hg.
3. Take overhead into lights receiver. This is the 1st cut (lights or phenol cut). Continue this cut as long as the overhead vapor temperature is less than 180° C.
4. When overhead vapor temperature reaches 180° C., start 2nd cut (intermediate cut). Raise still (18) pot temperature to 210° C. Take this cut for about one hour of good flow.
5. After intermediate cut raise still (18) temperature to 220° C. The DPC or 3rd cut is taken into an agitated receiver 34. Take DPC or 3rd cut until overhead vapor temperature drops below 180° C. or rises above 190° C.
6. After all DPC is collected, break vacuum, cool and flake the third or DPC cut.
7. After DPC cut (3rd cut) is collected, take 2nd cut from receiver (32) (intermediate cut) cool and flake. Save this cut for reprocessing in a future batch with new crude DPC.

In the distillation embodiment shown in the drawing, the following temperatures are advantageous:

Receiver (28, 32, 34) temperatures circa 90° C.

Vapor condenser (30) temperature circa 90° C.

Transfer lines to flaker (38) temperature circa 100° C.

The following Table 2 shows the distillation cuts or fractions taken and the compositional make-up of each cut.

TABLE 2

| | OVERHEAD VAPOR TEMPERATURE | APPROX. WT. (lbs) | APPROX. COMPOSITION |
|---|---|---|---|
| DPC (washed 3×) Charged to still | — | 727 ± 20 | 97 ± 1% DPC .6 ± .1% OOH .5% $H_2O$ |
| 1st cut (Lights cut) | <180° C. | 10 ± 5 | mostly water, phenol and some entrained DPC. |
| 2nd cut (Intermediate cut) | 180–185° C. | 75 ± 25 | 95 ± 1% DPC 4 ± 1% OOH 1% Uncal. |
| 3rd cut (Product cut) | 180–190° C. | 550 ± 50 | 99.6 ± 2% DPC .06 ± .01% OOH Remainder uncal. <1 ppm iron |
| Tar Residue | — | 12.5 ± 7 | 35 ± 5% DPC .07 ± .02% OOH 65 ± 5% Uncal. |

TABLE 2-continued

| OVERHEAD VAPOR TEMPERATURE | APPROX. WT. (lbs) | APPROX. COMPOSITION |
|---|---|---|

The purpose of the second cut is to assure that when the product cut is taken, it is well into purified DPC flow. The amount taken over in the 2nd cut is dictated in part by time (circa 1 hour of flow).

From the Table 2 supra., it may be seen that the process of the invention for purification of diaryl carbonates can produce a consistently good quality diphenyl carbonate assuming typical quality crude from commercial processes of preparation as the starting material.

I claim:

1. A process for the purification of diphenyl carbonate contaminated with compounds affecting color or reactivity of the carbonate in polymerizations, which comprises;
   1) washing a molten form of the diphenyl carbonate a plurality of times, with water at a temperature to maintain the molten form; and
   2) fractionally distilling the washed diphenyl carbonate so as to separate from the washed diphenyl carbonate,
      (a) a first, phenol cut;
      (b) a second, partially purified diphenyl carbonate cut; and
      (c) a third, purified diphenyl carbonate cut.

2. A process of claim 1 wherein the temperature of the wash water is within the range of from 75° C. to 95° C.

3. A process of claim 2 wherein there are 2 to 4 washes.

4. A process of claim 3 wherein there are 3 washes.

5. A process of claim 1 wherein the first phenol cut is taken at an overhead vapor temperature of less than 180° C.

6. A process of claim 5 wherein the second, partially purified diphenyl carbonate cut is taken at an overhead vapor temperature within the range of from 180° C. to 190° C. for about 1 hour.

7. A process of claim 6 wherein the third cut is taken at an overhead vapor temperature within the range of from 180° C. to 190° C.

8. A process of claim 6 wherein the second partially purified diphenyl carbonate cut is recycled and mixed with diphenyl carbonate and the resulting mixture is subjected to purification by process steps 1) and 2).

* * * * *